US010252783B2

(12) United States Patent
Salters et al.

(10) Patent No.: US 10,252,783 B2
(45) Date of Patent: Apr. 9, 2019

(54) SAFETY IMPROVEMENTS FOR UV RADIATION IN AQUATIC APPLICATIONS

(71) Applicant: KONINKLIJKE PHILIPS N.V., Eindhoven (NL)

(72) Inventors: Bart Andre Salters, Eindhoven (NL); Roelant Boudewijn Hietbrink, Utrecht (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 15/577,579

(22) PCT Filed: May 11, 2016

(86) PCT No.: PCT/EP2016/060592
§ 371 (c)(1),
(2) Date: Nov. 28, 2017

(87) PCT Pub. No.: WO2016/192942
PCT Pub. Date: Dec. 8, 2016

(65) Prior Publication Data
US 2018/0134351 A1 May 17, 2018

(30) Foreign Application Priority Data
Jun. 3, 2015 (EP) .................. 15170615.7

(51) Int. Cl.
*A61L 2/10* (2006.01)
*B63B 59/04* (2006.01)
(Continued)

(52) U.S. Cl.
CPC ............ *B63B 59/04* (2013.01); *A61L 2/10* (2013.01); *B08B 17/02* (2013.01); *C02F 1/325* (2013.01);
(Continued)

(58) Field of Classification Search
CPC ... B63B 59/04; A61L 2/08; A61L 2/10; A61L 2202/14; B08B 17/02; C02F 1/32;
(Continued)

(56) References Cited

U.S. PATENT DOCUMENTS 5,308,505 A * 5/1994 Titus .................. A61L 2/0011
210/745
6,579,495 B1 6/2003 Maiden
(Continued)

FOREIGN PATENT DOCUMENTS

DE 102010052446 A1 2/2012
GB 1332462 A 10/1973
(Continued)

OTHER PUBLICATIONS

Yebra, D. M. et al., "Antifouling technology-past, present and future steps towards efficient and environmentally friendly antifouling coatings", Progress in Organic Coatings, Elsevier BV, NL, vol. 50, Jan. 1, 2004, pp. 75-104.

*Primary Examiner* — David E Smith

(57) ABSTRACT

The invention provides an object (10) that during use is at least partly submerged in water, the object (10) further comprising an anti-biofouling system (200) comprising an UV emitting element (210), wherein the UV emitting element (210) is configured to irradiate with UV radiation (221) during an irradiation stage one or more of (i) a part (111) of an external surface (11) of said object (10) and (ii) water adjacent to said part (111) of said external surface (11), wherein the light source (220) is at least controllable between a first UV radiation level and a second UV radiation level, wherein the first UV radiation level is larger than the second UV radiation level, wherein the object (10) is selected from the group consisting of a vessel (1) and an infrastructural object (15), wherein the object (10) further comprises a control system (300) configured to control said
(Continued)

UV radiation (221) as function of input information comprising information of one or more of (i) a location of the object (10), (ii) movement of the object (10), (iii) a distance (d) of the object (10) to a second object (20), and (iv) a position of the part (111) of the external surface (11) relative to the water.

15 Claims, 5 Drawing Sheets

(51) Int. Cl.
  *B08B 17/02* (2006.01)
  *C02F 1/32* (2006.01)
(52) U.S. Cl.
  CPC ..... *A61L 2202/14* (2013.01); *C02F 2201/326* (2013.01); *C02F 2201/3227* (2013.01); *C02F 2303/20* (2013.01)
(58) Field of Classification Search
  CPC .............. C02F 1/325; C02F 2201/3227; C02F 2201/326; C02F 2303/20
  See application file for complete search history.

(56) References Cited

U.S. PATENT DOCUMENTS

| | | |
|---|---|---|
| 6,656,424 B1 | 12/2003 | Deal |
| 8,779,391 B2 | 7/2014 | Flaherty et al. |
| 8,791,441 B1 | 7/2014 | Lichtblau |
| 2010/0199906 A1* | 8/2010 | Stieglitz ................. A01K 79/02 114/219 |
| 2012/0144569 A1 | 6/2012 | Kodat |
| 2013/0048877 A1* | 2/2013 | Thoren .................. G02B 6/102 250/492.1 |
| 2014/0196745 A1* | 7/2014 | Whelan .................. B63B 59/04 134/1 |

FOREIGN PATENT DOCUMENTS

| | | |
|---|---|---|
| JP | 11278374 A | 10/1999 |
| WO | 2014188347 A1 | 11/2014 |

* cited by examiner

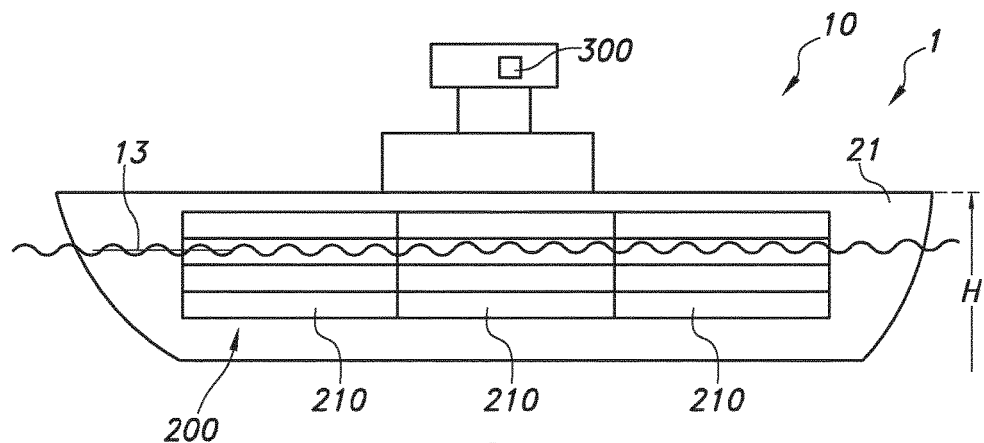
FIG. 2F
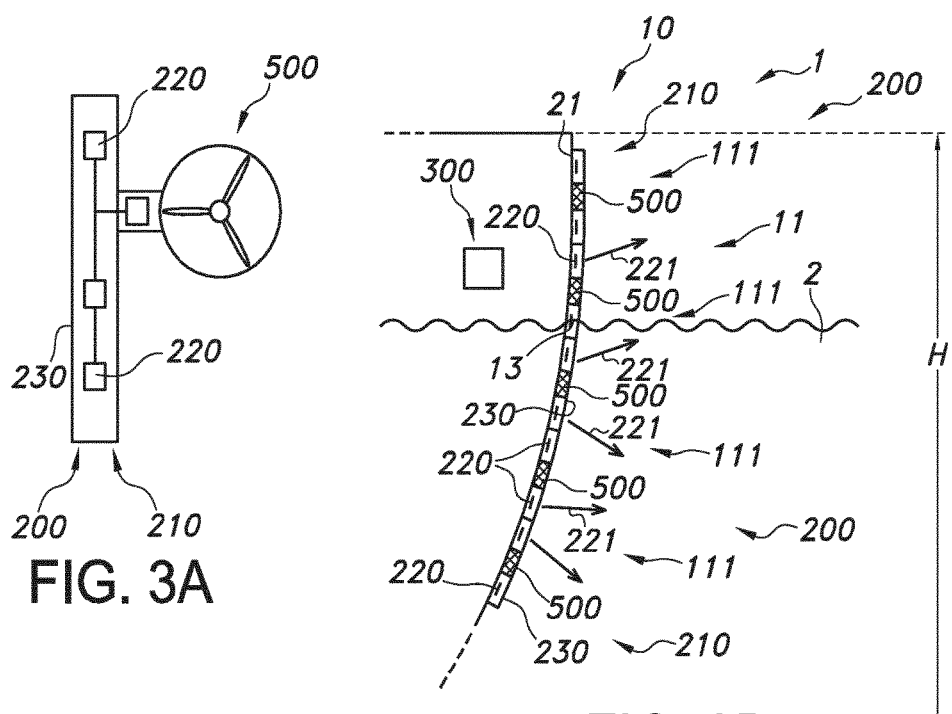
FIG. 3A
FIG. 3B

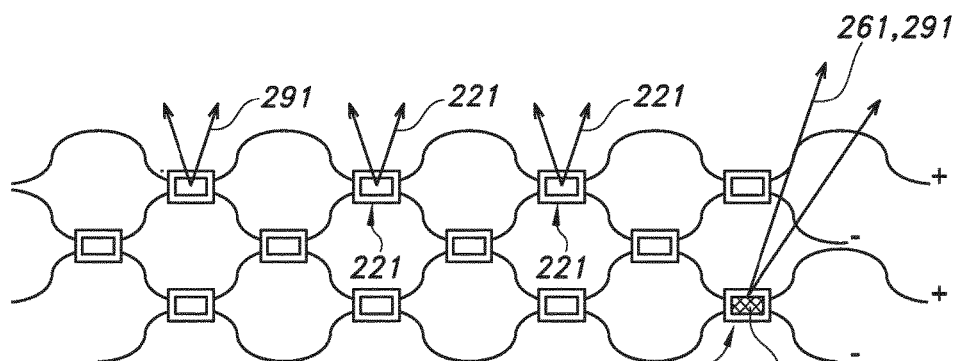
FIG. 4A
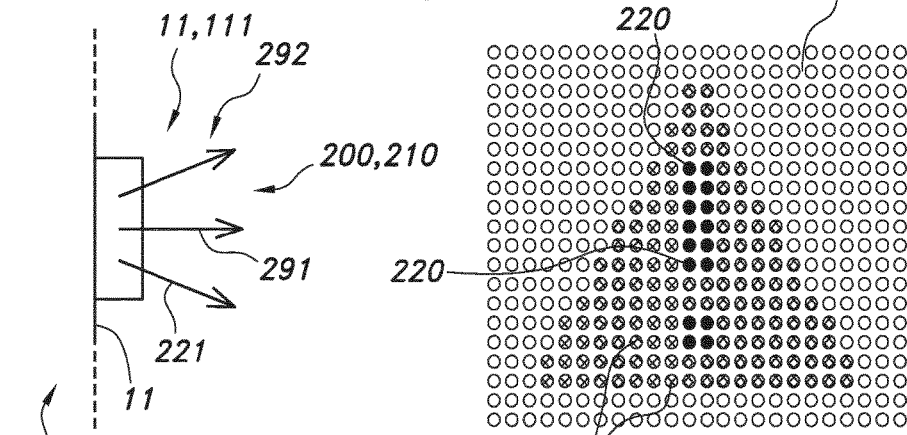
FIG. 4B
FIG. 4C
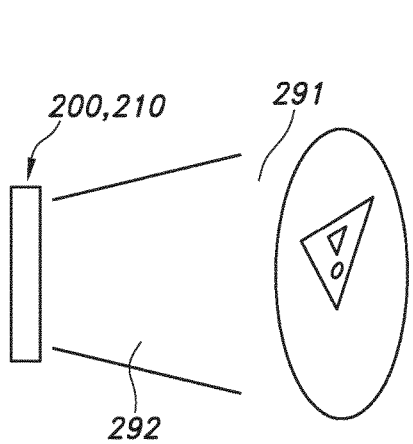
FIG. 4D
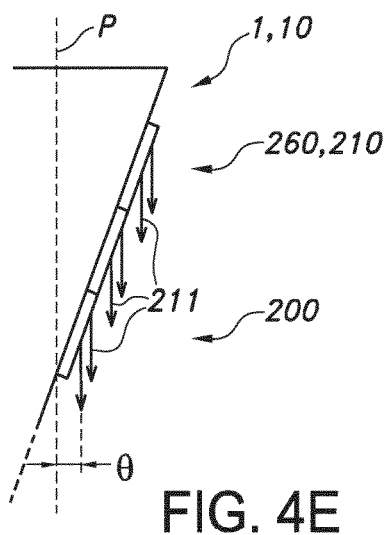
FIG. 4E

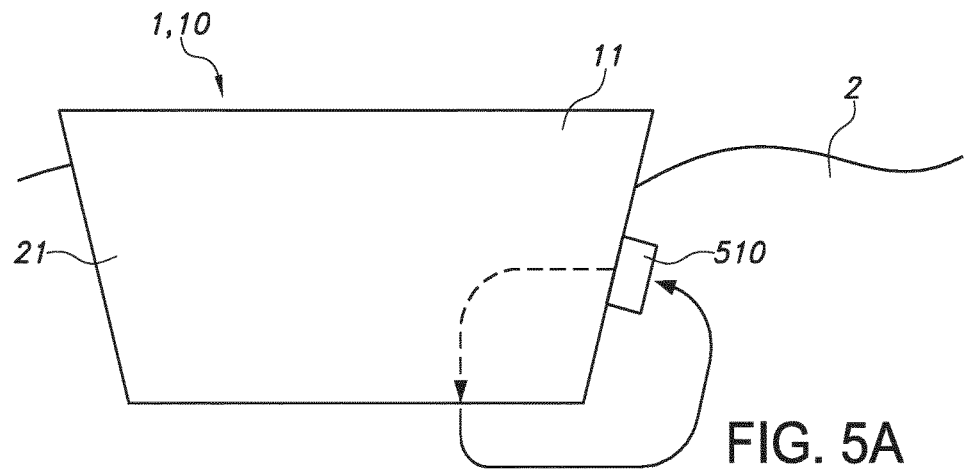
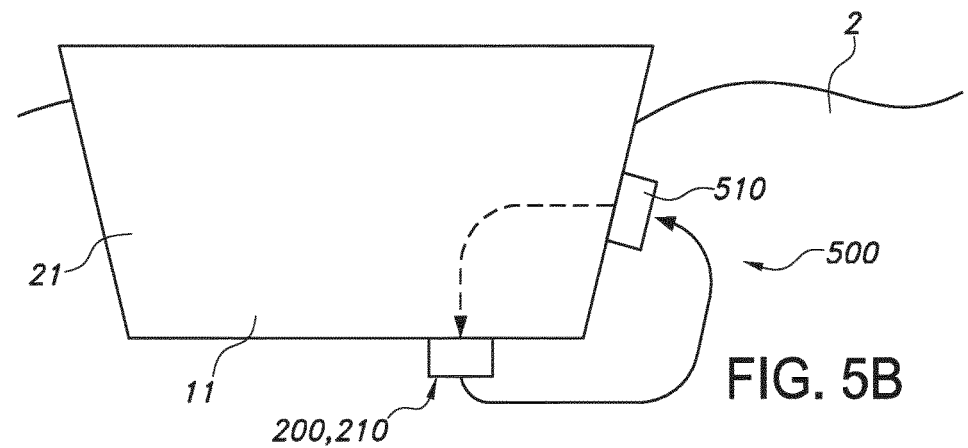
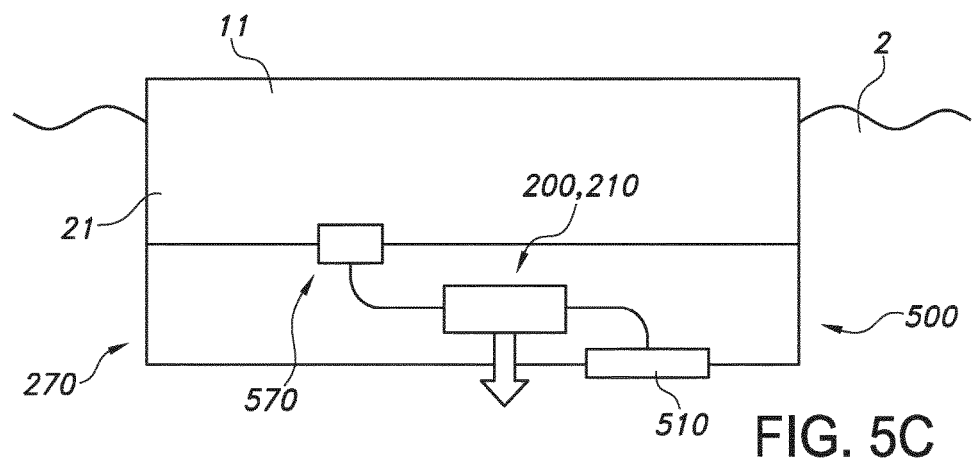

SAFETY IMPROVEMENTS FOR UV RADIATION IN AQUATIC APPLICATIONS

CROSS-REFERENCE TO PRIOR APPLICATIONS

This application is the U.S. National Phase application under 35 U.S.C. § 371 of International Application No. PCT/EP2016/060592, filed on 11 May 2016, which claims the benefit of European Patent Application No. 15170615.7, filed on 3 Jun. 2015. These applications are hereby incorporated by reference herein.

FIELD OF THE INVENTION

The invention relates to an object that during use is at least partly submerged in water, especially a vessel or an infrastructural object.

BACKGROUND OF THE INVENTION

Anti-biofouling methods are known in the art. US2013/0048877, for instance, describes a system for anti-biofouling a protected surface, comprising an ultraviolet light source configured to generate ultraviolet light, and an optical medium disposed proximate to the protected surface and coupled to receive the ultraviolet light, wherein the optical medium has a thickness direction perpendicular to the protected surface, wherein two orthogonal directions of the optical medium orthogonal to the thickness direction are parallel to the protected surface, wherein the optical medium is configured to provide a propagation path of the ultraviolet light such that the ultraviolet light travels within the optical medium in at least one of the two orthogonal directions orthogonal to the thickness direction, and such that, at points along a surface of the optical medium, respective portions of the ultraviolet light escape the optical medium.

SUMMARY OF THE INVENTION

Biofouling or biological fouling (herein also indicated as "fouling") is the accumulation of microorganisms, plants, algae, and/or animals on surfaces. The variety among biofouling organisms is highly diverse and extends far beyond attachment of barnacles and seaweeds. According to some estimates, over 1700 species comprising over 4000 organisms are responsible for biofouling. Biofouling is divided into microfouling which includes biofilm formation and bacterial adhesion, and macrofouling which is the attachment of larger organisms. Due to the distinct chemistry and biology that determine what prevents organisms from settling, these organisms are also classified as hard or soft fouling types. Calcareous (hard) fouling organisms include barnacles, encrusting bryozoans, mollusks, polychaete and other tube worms, and zebra mussels. Examples of non-calcareous (soft) fouling organisms are seaweed, hydroids, algae and biofilm "slime". Together, these organisms form a fouling community.

In several circumstances biofouling creates substantial problems. Machinery stops working, water inlets get clogged, and hulls of ships suffer from increased drag. Hence the topic of anti-fouling, i.e. the process of removing or preventing fouling from forming, is well known. In industrial processes, bio-dispersants can be used to control biofouling. In less controlled environments, organisms are killed or repelled with coatings using biocides, thermal treatments or pulses of energy. Non-toxic mechanical strategies that prevent organisms from attaching include choosing a material or coating with a slippery surface, or creation of nanoscale surface topologies similar to the skin of sharks and dolphins which only offer poor anchor points. Biofouling on the hull of ships causes a severe increase in drag, and thus increased fuel consumption. It is estimated that an increase of up to 40% in fuel consumption can be attributed to biofouling. As large oil tankers or container transport ships can consume up to €200.000 a day in fuel, substantial savings are possible with an effective method of anti-biofouling.

It surprisingly appears that one may effectively use UV radiation to substantially prevent biofouling on surfaces that are in contact with sea water or water in lakes, rivers, canals, etc. Herewith, an approach is presented based on optical methods, in particular using ultra-violet light or radiation (UV). It appears that most micro-organisms are killed, rendered inactive or unable to reproduce with sufficient UV light. This effect is mainly governed by the total dose of UV light. A typical dose to kill 90% of a certain micro-organism is 10 mW/h/m$^2$. However, in most of these embodiments, there may be some UV radiation that may reach places it is not intended to go. This basically covers everything above the waterline, and especially human beings in close proximity to the aquatic application. During cruise at open sea, this may not happen (even though it is to be mentioned that personnel on board of the vessel might still face a (tiny) risk), but while e.g. being docked in a harbor the risk is larger, as more people move near the boat. This can include dock workers, crane operators, supply vessels mooring near the ship (on the non-dock side), etc.

Hence, it is an aspect of the invention to provide an alternative system or method for prevention or reduction of biofouling, which preferably further at least partly obviates one or more of above-described drawbacks.

In a first aspect, the invention provides an object that during use is at least partly submerged in water, the object further comprising an anti-biofouling system (which may also be indicated as "anti-fouling lighting system") comprising an UV emitting element for application of UV radiation (which may also be indicated as "anti-fouling light") (to a part of an external surface of the object), wherein the UV emitting element especially comprises one or more light sources, even more especially one or more solid state light sources, and is configured to irradiate with said UV radiation (during an irradiation stage) one or more of (i) a (said) part of said external surface and (ii) water adjacent to said part of said external surface, wherein the object is especially selected from the group consisting of a vessel and an infrastructural object.

In yet a further aspect, the invention also provides the anti-biofouling system per se, i.e. an anti-biofouling system comprising an UV emitting element for application of UV radiation (to a part of an external surface of the object), wherein the UV emitting element comprises one or more light sources and is configured to irradiate with said UV radiation (during an irradiation stage) one or more of (i) said part of said external surface and (ii) water adjacent to said part of said external surface. The invention is further especially explained with reference to the bio-antifouling system in combination with the object.

Especially, the object, or the anti-biofouling system, comprise(s) a control system. Hence, the object comprises such comprises such control system, which may optionally be integrated in the anti-biofouling system, or elsewhere in the object. In a specific embodiment, the control system is especially configured to control said UV radiation as function of input information comprising information of one or more of (i) a location of the object, (ii) movement of the object, (iii) a distance (d) of (said part of) the object to a second object, and (iv) a position of the part of the external surface relative to the water. Hence, especially the anti-biofouling system is configured to control said UV radiation as function of input information comprising information of a human UV radiation exposure risk.

With such bio-antifouling system the UV radiation may be minimized in situations or applications wherein UV radiation may be considered risky, whereas in situations or applications wherein the application of UV radiation is less risky or not risky, the UV radiation may be applied. For instance, the biofouling unit may be configured to provide UV radiation only at open sea, or when the object is moving at cruise speed, or when no people are detected in the vicinity of the object or bio-antifouling system, or when the relevant part of the bio-antifouling system is below the water line (see further also below).

Herein, the phrase "object that during use is at least partly submerged in water" especially refers to objects such as vessels and infrastructural objects that have aquatic applications. Hence, during use such object will be in general in contact with the water, like a vessel in the sea, a lake, a canal, a river, or another waterway, etc. The term "vessel" may e.g. refer to e.g. a boat or a ship, etc., such as a sail boat, a tanker, a cruise ship, a yacht, a ferry, a submarine, etc. etc. The term "infrastructural object" may especially refer to aquatic applications that are in general arranged substantially stationary, such as a dam, a sluice, a pontoon, an oilrig, etc. etc. The term "infrastructural object" may also refer pipes (for e.g. pumping up ocean water to e.g. a power plant), and other parts of (hydro-electrical) power plants, such as cooling systems, turbines, etc. The term "external surface" especially refers to the surface that may be in physical contact with water. In the case of pipes this may apply to one or more of the internal pipe surface and the external pipe surface. Hence, instead of the term "external surface" also the term "fouling surface" may be applied. Further, in such embodiments the term "water line" may also refer to e.g. filling level. Especially, the object is an object configured for marine applications, i.e. application in or near to a sea or an ocean. Such objects are during their use at least temporarily, or substantially always, at least partly in contact with the water. The object may be at least partly below the water (line) during use, or may substantially be all of its time below the water (line), such as for submarine applications.

Due to this contact with the water, biofouling may occur, with the above indicated disadvantages. Biofouling will occur at the surface of an external surface ("surface") of such object. The surface of an (element of the) object to be protected may comprise steel, but may optionally also comprise another material, such as e.g. selected from the group consisting of wood, polyester, composite, aluminium, rubber, hypalon, PVC, glass fiber, etc. Hence, instead of a steel hull, the hull may also be a PVC hull or a polyester hull, etc. Instead of steel, also another iron material, such as an (other) iron alloys may be used Herein, the term "fouling" or "biofouling" or "biological fouling" are interchangeably used. Above, some examples of fouling are provided. Biofouling may occur on any surface in water, or close to water and being temporarily exposed to water (or another electrically conductive aqueous liquid). On such surface biofouling may occur when the element is in, or near water, such as (just) above the water line (like e.g. due to splashing water, such as for instance due to a bow wave). Between the tropics, biofouling may occur within hours. Even at moderate temperatures, the first (stages of) fouling will occur within hours; as a first (molecular) level of sugars and bacteria.

The anti-biofouling system comprises at least an UV emitting element. Further, the anti-biofouling system may comprise a control system (see also below), an electrical energy supply, such as a local energy harvesting system (see also below), etc.

The term "anti-biofouling system" may also refer to a plurality of such systems, optionally functionally coupled to each other, such as e.g. controlled via a single control system. Further, the anti-biofouling system may comprise a plurality of such UV emitting elements. Herein, the term "UV emitting element" may (thus) refer to a plurality of UV emitting elements. For instance, in an embodiment a plurality of UV emitting elements may be associated to an external surface of the object, such as a hull, or may be comprised by such surface (see also below), whereas e.g. a control system may be configured somewhere within the object, such as in a control room or wheel house of a vessel.

The surface or area on which fouling may be generated is herein also indicated as fouling surface. It may e.g. be the hull of a ship and/or an emission surface of an optical medium (see also below). To this end, the UV emitting element provides UV radiation (anti-fouling light) that is applied to prevent formation of biofouling and/or to remove biofouling. This UV radiation (anti-fouling light) especially at least comprises UV radiation (also indicated as "UV light"). Hence, the UV emitting element is especially configured to provide UV radiation. Thereto, the UV emitting element comprises a light source. The term "light source" may also relate to a plurality of light sources, such as 2-20 (solid state) LED light sources, though many more light sources may also be applied. Hence, the term LED may also refer to a plurality of LEDs. Especially, the UV emitting element may comprise a plurality of light sources. Hence, as indicated above, the UV emitting element comprises one or more (solid state) state light sources. The LEDs may be (OLEDs or) solid state LEDs (or a combination of these LEDs). Especially, the light source comprises solid state LEDs. Hence, especially, the light source comprises a UV LED configured to provide one or more of UV-A and UVC light (see also below). UV-A may be used to impair cell walls, whereas UVC may be used to impair DNA. Hence, the light source is especially configured to provide the UV radiation. Herein, the term "light source" especially refers to a solid state light source.

Ultraviolet (UV) is that part of electromagnetic light bounded by the lower wavelength extreme of the visible spectrum and the X-ray radiation band. The spectral range of UV light is, by definition between about 100 and 400 nm (1 nm=$10^{-9}$ m) and is invisible to human eyes. Using the CIE classification the UV spectrum is subdivided into three bands: UVA (long-wave) from 315 to 400 nm; UVB (medium-wave) from 280 to 315 nm; and UVC (short-wave) from 100 to 280 nm. In reality many photobiologists often speak of skin effects resulting from UV exposure as the weighted effect of wavelength above and below 320 nm, hence offering an alternative definition.

A strong germicidal effect is provided by the light in the short-wave UVC band. In addition erythema (reddening of the skin) and conjunctivitis (inflammation of the mucous membranes of the eye) can also be caused by this form of light. Because of this, when germicidal UV-light lamps are used, it is important to design systems to exclude UVC leakage and so avoid these effects. In case of immersed light sources, absorption of UV light by water may be strong enough that UVC leaking is no problem for humans above the liquid surface. Hence, in an embodiment the UV radiation (anti-fouling light) comprises UVC light. In yet another embodiment, the UV radiation comprises radiation selected from a wavelength range of 100-300 nm, especially 200-300 nm, such as 230-300 nm. Hence, the UV radiation may especially be selected from UVC and other UV radiation up to a wavelength of about 300 nm. Good results are obtained with wavelengths within the range of 100-300 nm, such as 200-300 nm.

As indicated above, the UV emitting element is configured to irradiate with said UV radiation (during an irradiation stage) one or more of (i) said part of said external surface and (ii) water adjacent to said part of said external surface. The term "part" refers to part of the external surface of an object, such as e.g. a hull or a sluice (door). However the term "part" may also refer to substantially the entire external surface, such as the external surface of the hull or sluice. Especially, the external surface may comprise a plurality of parts, which may be irradiated with the UV light of one or more light sources, or which may be irradiated with the UV radiation of one or more UV emitting elements. Each UV emitting element may irradiate one or more parts. Further, there may optionally be parts that receive UV radiation of two or more UV emitting elements.

In general, there may be distinguished between two main embodiments. One of the embodiments includes the part of the external surface being irradiated with the UV radiation with between the light source and UV emitting element water (or air when above the water line), such as sea water, at least during the irradiation stage. In such embodiment, the part is especially comprised by the "original" external surface of the object. However, in yet another embodiment, the "original" external surface may be extended with a module, especially a relatively flat module, that is attached to the "original" external surface of the object (such as the hull of a vessel), whereby the module itself forms in fact the external surface. For instance, such module may be associated to the hull of a vessel, whereby the module forms (at least part of) the external surface. In both embodiments the UV emitting element especially comprises a radiating exit surface (see further also below). However, especially in the latter embodiment wherein the UV emitting element may provide part of said external surface, such radiation escape surface may provide the part (as the first part and the radiation escape surface may essentially coincide; especially may be the same surface).

Hence, in an embodiment the UV emitting element is attached to said external surface. In yet a further specific embodiment the radiation escape surface of the anti-biofouling system is configured as part of said external surface. Hence, in some of the embodiments the object may comprise a vessel comprising a hull, and the UV emitting element is attached to said hull. The term "radiation escape surface" may also refer to a plurality of radiation escape surfaces (see also below).

In both general embodiments, the UV emitting element is configured to irradiate with said UV radiation (during an irradiation stage) water adjacent to said part of said external surface. In the embodiments wherein the module itself forms in fact the external surface, the UV emitting element is at least configured to irradiate with said UV radiation (during an irradiation stage) said part of said external surface, as it is in fact part of said external surface, and optionally also water adjacent to said part of said external surface. Hereby, biofouling may be prevented and/or reduced.

In an embodiment, a significant amount of a protected surface to be kept clean from fouling, preferably the entire protected surface, e.g. the hull of a ship, may be covered with a layer that emits germicidal light ("anti-fouling light"), in particular UV light.

In yet another embodiment, the UV radiation (anti-fouling light) may be provided to the surface to be protected via a waveguide, such as a fiber.

Hence, in an embodiment the anti-fouling lighting system may comprise an optical medium, wherein the optical medium comprises a waveguide, such as an optical fiber, configured to provide said UV radiation (anti-fouling light) to the fouling surface. The surface of e.g. the waveguide from which the UV radiation (anti-fouling light) escapes is herein also indicated as emission surface. In general, this part of the waveguide may at least temporarily be submerged. Due to the UV radiation (anti-fouling light) escaping from the emission surface, an element of the object that is during use at least temporarily exposed to the liquid (such as seawater), may be irradiated, and thereby anti-fouled. However, the emission surface per se may also be anti-fouled. This effect is used in some of the embodiments of the UV emitting element comprising an optical medium described below.

Embodiments with optical media are also described in WO2014188347. The embodiments in WO2014188347 are herein also incorporated by reference as they are combinable with the control unit and/or water switch, and other embodiments, described herein.

As indicated above, the UV emitting element may especially comprise a UV radiation escape surface. Hence, in a specific embodiment the UV emitting element comprises a UV radiation escape surface, with the UV emitting element especially being configured to provide said UV radiation downstream from said UV radiation escape surface of said UV emitting element. Such UV radiation escape surface may be an optical window through which the radiation escapes from the UV emitting element. Alternatively or additionally, the UV radiation escape surface may be the surface of a waveguide. Hence, UV radiation may be coupled in the UV emitting element into the waveguide, and escape from the element via a (part of a) face of the waveguide. As also indicated above, in embodiments the radiation escape surface may optionally be configured as part of the external surface of the object.

The terms "upstream" and "downstream" relate to an arrangement of items or features relative to the propagation of the light from a light generating means (here the especially the first light source), wherein relative to a first position within a beam of light from the light generating means, a second position in the beam of light closer to the light generating means is "upstream", and a third position within the beam of light further away from the light generating means is "downstream".

Especially, the (solid state) light source is at least controllable between a first UV radiation level and a second UV radiation level, wherein the first UV radiation level is larger than the second UV radiation level (and wherein the second UV radiation level is smaller than the first radiation level or may even be zero). Hence, in an embodiment the light source can be switched off and can be switched on (during a radiation stage). Further, optionally also the intensity of the UV radiation may be controlled between these two stages, such as a stepwise or continuous UV radiation intensity control. Hence, the light source is especially controllable (and thus its UV radiation intensity is).

As indicated above, the control system is especially configured to control said UV radiation as function of input information comprising of one or more of (i) a location of the object, (ii) movement of the object, (iii) a distance (d) of (said part of) the object to a second object, and (iv) a position of the part of the external surface relative to the water.

In an embodiment, wherein the control system may be configured to control the UV emitting element to the first UV radiation level when the location of the object complies with a first predetermined location, and to the second UV radiation level when the location of the object complies with a second predetermined location. For instance, based on location date, such as with the aid of satellite navigation, the location of the object can be know and the control system can then determine whether such location has an enhanced risk for UV exposure to e.g. humans, such as in a harbor, or a reduced (or no) risk, such as on a river or on the sea. The term "predetermined location" may also refer to a plurality of predetermined locations, such as geographical areas, like "open sea", "more than 1 mile offshore", etc.

In yet a further embodiment, the control system may be configured to control the UV emitting element to the first UV radiation level when the object has a velocity of at least a predetermined minimum velocity, and to the second UV radiation level when the velocity of the objects is below said predetermined minimum velocity. For instance, when the velocity of the object is zero, it is likely that the risk of UV exposure to humans may be higher, because the object may e.g. be in maintenance, or a vessel may be in a harbor or people may walk over a sluice, etc. etc. However, when the velocity is non-zero, or over a certain threshold, such risks will substantially be reduced as in general people will then not be in the vicinity of the relevant part(s) of the external surface (or only for short periods of time), which will in general be just above the water (line), at the waterline and below.

In yet a further embodiment, the control system may be configured to control the UV emitting element to the first UV radiation level when the distance (d) of the object to the second object meets at least a predefined threshold value, and to the second UV radiation level when the distance (d) of the object to the second object is below the predefined threshold value. The second object may be a human or any other living or non living object, in general having a volume of at least about 1 $dm^3$. In general, this embodiment may include a sensor, configured to sense other objects. Hence, the object or in an embodiment the anti-biofouling system (or both), may further comprise a sensor configured to sense one or more of (i) the second object and (ii) a movement of the second object and configured to generate a corresponding sensor signal, and wherein the control system is configured to control said UV radiation as function of said sensor signal. Hence, e.g. at open sea, or on a river, no second object may (often) be sensed, whereas e.g. in a harbor people may be sensed. In the former situation, the UV radiation may be applied; in the latter situation the UV radiation may be reduced or switched off. The sensor may e.g. include a thermal sensor or a motion sensor, etc. Further, the term "sensor" may also refer to a plurality of sensors, of which optionally two or more may be configured to sense different properties.

In an embodiment, the control system comprises a plurality of control systems. For instance, the vessel may comprise a control system, as master control system, with each anti-biofouling system comprising a slave control system. Optionally, the control system may be configured external form the object, i.e. remote from the object. In a specific embodiment, a master control system, remote from the object, controls the slave control system comprised by the object, (such as the anti-biofouling system). Hence, for instance the (master) control system may be far away; but not on the vessel, but ashore, such as in a control room of a shipping companies. Such master control system may be configured to control anti-biofouling systems of a plurality of objects.

A relative simple way to reduce the risk of undesired UV radiation exposure of humans may be apply UV radiation only below the water (line). Hence, in an embodiment the control system is configured to control the UV emitting element to the first UV radiation level when one or more of the part and the UV radiation escape surface are below the water (line), and to the second UV radiation level when one or more of the part and the UV radiation escape surface are above the water (line). This may include the use of one or more of (i) a sensor configured to sense the water (line), and (ii) information about loading. Based thereon, the control system may decide whether or not the UV radiation can be applied or will be applied substantially only to the part of the external surface that is below the water (line). Note that in this embodiment there may still be a plurality of variants as the radiation may in general then only be applied when the part is below the water (line), but optionally the UV radiation escape surface may be above the water (line), or also below the water (line). In the latter variant, risk may even be further minimized. Hence, especially the control system is configured to control the UV emitting element to the first UV radiation level when the UV radiation escape surface is below the water (line) and to the second UV radiation level when the UV radiation escape surface is above the water (line). Alternatively or additionally, especially in an embodiment the control system is configured to control the UV emitting element to the first UV radiation level when the part (and the UV radiation escape surface is below the water (i.e. especially the water line), and to the second UV radiation level when the part is above the water (i.e. especially the water line). When using a sensor configured to sense the water, such sensor may be configured close to the radiation escape surface, but configured higher, such as at least 10 cm higher, especially at least 20 cm higher, such as in the range of 10-100 cm higher, like 20-50 cm higher (relative to the object during use) than said surface. In this way, the UV radiation may only be generated when the sensor, and thus the radiation escape surface, is below the water (line) (see further also below). In this way, it may thus be guaranteed that UV light will only be emitted at least e.g. 50 cm below the waterline; which is sufficient to absorb a substantial part of the light. Depending on the absolute intensity of the 'on' level, a lower or higher value than 50 cm may be designed, such as to achieve an inherently safe system.

As indicated above, the object or the anti-biofouling system may comprise a plurality of radiation escape surfaces. In embodiments this may refer to a plurality of anti-biofouling systems. However, alternatively or additionally, in embodiments this may refer to an anti-biofouling system comprising a plurality of UV radiation emitting elements. Such anti-biofouling system may thus especially include a plurality of light sources for providing UV radiation. However, alternatively or additionally, in embodiments this may (also) refer to an UV emitting element comprising a plurality of light sources configured to provide the UV radiation. Note that an UV emitting element with a single UV radiation escape surface may (still) include a plurality of light sources.

Especially when the UV emitting element comprises a plurality of light sources and a plurality of UV radiation escape surfaces, especially with each of such surface addressed by one more light sources, and/or when the bio-fouling system comprises a plurality of UV emitting elements, by a control of the light sources it is possible to address different parts of the external surface independently. Hence, by arranging the different UV radiation escape surfaces at different heights of the object (with the height especially defined during use of the object), it is possible to substantially only irradiate with UV radiation only those parts for which applies that one or more of the part and the UV radiation escape surface are below the water (line).

Hence, in a specific embodiment the anti-biofouling system comprises a plurality of light sources, a plurality of radiation escape surfaces, and a plurality of said parts, wherein the plurality of light sources are configured to provide said UV radiation via said plurality of radiation escape surfaces to said plurality of parts, and wherein said plurality of parts are configured at different heights of the object. Especially, the control system may be configured to control the (solid state) light sources individually as function of said input information. For instance, in a specific embodiment the control system may be configured to control the light sources individually as function of the positions of the parts of the external surface relative to the water (i.e. the water line). For instance, the anti-bio fouling system may comprise a sensor or another element to sense water in the vicinity of the relevant radiation escape surface and/or part. It is noted again that in some embodiments the radiation escape surface may comprise the part. Alternatively or additionally, the input information comprising information of the position of the external surface relative to the water is based on a loading of the vessel. Also in this way, the control system may control the UV radiation, e.g. as function of e.g. the positions of the parts of the external surface relative to the water. Alternatively or additionally, the control system may control the UV radiation, e.g. as function of e.g. the positions of UV radiation escape surfaces relative to the water. However, the control system may also be configured to calculate the draft (draught) of the object, especially when the object is a vessel, and/or receive from an external source information about the draft. Hence, in a further embodiment the input information comprises a calculated draft of the object. In other embodiments, wherein the object is not a vessel, the input information comprising information of the position of the external surface relative to the water may be based on a water line (or water level) relative to the infrastructural object.

For vessels, waves might make for a rapidly changing water line and for infrastructure objects, optionally the tides (or a filling level) may make a difference in the water line. Hence, especially the control unit and the optional sensor are configured (to be able) to follow these changes. For instance, the sensor may be configured to sense continuously, or periodically with a frequency able to follow such changes.

In yet a further specific embodiment, the object further comprises a water switch, wherein the anti-biofouling system is configured to provide said UV radiation to said part when the water switch is in physical contact with the water, especially electrically conductive water, such as sea water. The water switch is especially herein defined as an electrical switch which upon contact with the water may switch an electrical device on or off, especially switch on. Hence, the water switch is especially an electrical water switch. The term "water switch" may also refer to a plurality of water switches. In general each water switch may functionally be coupled to a single light source or to a subset of light sources or to a UV emitting element or to a subset of UV emitting elements.

A further advantage of a water switch may e.g. be in combination with a control system. Such control system may e.g. instruct the UV emitting element to provide UV radiation. The water switch may then be an additional safety valve, only actually allowing providing UV radiation when the water switch is in physical contact with water. Hence, in a further aspect the invention provides an object that during use is at least partly submerged in water, the object further comprising an anti-biofouling system comprising an UV emitting element, wherein the UV emitting element comprises one or more light sources and is configured to irradiate with UV radiation during an irradiation stage one or more of (i) a part of a (said) external surface of said object and (ii) water adjacent to said part of said external surface, wherein the object is selected from the group consisting of a vessel and an infrastructural object, wherein the object further comprises a water switch, wherein the anti-biofouling system is configured to provide said UV radiation to said part in dependence of the water switch being in physical contact with the water.

Especially e.g. the part and the water switch may be configured at a same height. In this way, when the part is submerged, the water switch may switch on the UV emitting element, whereas when the part is not submerged, the water switch may switch of the UV emitting element. With such bio-antifouling system the UV radiation may be minimized in situations or applications wherein UV radiation may be considered risky, whereas in situations or applications wherein the application of UV radiation is less risky or not risky, the UV radiation may be applied. As indicated above, the anti-biofouling system may comprises a plurality of light sources, a plurality of radiation escape surfaces, and a plurality of said parts, wherein the plurality of light sources are configured to provide said UV radiation via said plurality of radiation escape surfaces to said plurality of parts, and wherein said plurality of parts are configured at different heights of the object. Further, especially the anti-biofouling system may further comprise a plurality of said water switches, configured at the heights of the plurality of parts, and wherein the anti-biofouling system is configured to provide said UV radiation to said parts when the respective water switches are in physical contact with the (electrically conductive) water. Hence, in this way, substantially irrespective of the draft or the water (line), the desired safety can be guaranteed as only UV radiation will be provided to the external surface parts that are below the water (line). Hence, the object may include a plurality of UV emitting elements, configured at different heights. Further, the object may comprise a plurality of water switches, also configured at different heights and configured to switch on the light source(s) of the respective UV emitting elements at substantially the same height as the water switches. In an embodiment, the object may comprise a plurality of UV emitting elements, applied at different heights of the external surface, and a plurality of water switches arranged at different heights, wherein the UV-emitting elements and water switches are functionally connected, wherein the heights are defined relative to the external surface during use of the object, wherein the anti-biofouling system is configured to provide said UV radiation with one or more UV emitting elements in dependence of the related one or more water-switches being in physical contact with electrically conductive water.

When using a water switch, such water switch may be configured close to the radiation escape surface, but configured higher, such as at least 10 cm higher, especially at least 20 cm higher, such as in the range of 10-100 cm higher, like 20-50 cm higher (relative to the object during use) than said surface. In this way, the UV radiation may only be generated when the water switch, and thus the radiation escape surface, is below the water (line) (see further also below).

In this way, it may thus be guaranteed that UV light will only be emitted at least e.g. 50 cm below the waterline; which is sufficient to absorb a substantial part of the light. Depending on the absolute intensity of the 'on' level, a lower or higher value than 50 cm may be designed, such as to achieve an inherently safe system.

The water switch may in an embodiment be configured to close an electronic circuit when physically being in contact with (electrically) conductive water. In an alternative or additional embodiment, the water switch may include a sensor configured to sense water and configured to provide a sensor signal when the sensor is physically in contact with water.

In yet a further embodiment, the object or the anti-biofouling system may further comprise a local energy harvesting system configured to harvest electrical energy and to provide said energy to said anti-biofouling system. In this way, e.g. the anti-biofouling system may be substantially independent of the mains, even e.g. a local mains on a vessel. In a specific embodiment, the local energy harvesting system may be comprised by said anti-biofouling system. In an embodiment, the local energy harvesting system is selected from the group consisting of a solar cell, a turbine operating in water, a piezoelectric element operating on a pressure of waves, etc. etc.

For instance, in an embodiment solar cells may be configured at the freeboard, and the UV emitting elements may be configured below the freeboard.

In yet another embodiment, the turbine and/or element that can derive energy from flow of water or pressure changes due to water movements, etc., as well as the UV emitting element are configured below the freeboard.

The term "local energy harvesting system" may also refer to a plurality of such local energy harvesting systems. Each of such local harvesting system may functionally be coupled with one or more anti-biofouling systems. Alternatively, each of such local harvesting system may functionally be coupled with one or more UV emitting elements. Especially, as also indicated above in relation to the water switches, especially the local energy harvesting systems may be configured at the heights of a plurality of parts or the UV radiation escape surface. In this way, only when the part and/or the UV radiation escape surface is submerged, especially when at least the UV radiation escape surface is submerged, energy can be harvested. In this way, automatically the UV radiation may only be switched on when the conditions are relatively safe.

In yet another embodiment, the energy can be harvested from water by the use of a sacrificial electrode. Especially, such a sacrificial electrode may be configured at the height of the part or of the UV radiation escape surface. In an embodiment, the local energy harvesting system comprises (i) a sacrificial electrode in electrical connection with a first electrode of the light source, and (ii) a second energy system electrode in electrical connection with a second electrode of the light source, wherein the energy system is configured to provide electrical power to said anti-biofouling system when the sacrificial electrode and the second energy system electrode are in electrical contact with the (electrically conductive) water. The term "sacrificial electrode" may also relate to a plurality of sacrificial electrodes.

Hence, in a further embodiment the sacrificial electrode is comprised by the water switch, wherein the anti-biofouling system is configured to provide said UV radiation to said part in dependence of the sacrificial electrode being in physical contact with the water. Hence, the water switch and energy harvesting system may be at least partially being integrated, with the sacrificial electrode being configured as sacrificial electrode and especially as necessary element in the water switch which may provide a closed electrical circuit only when the the sacrificial electrode is in physical contact with water.

In a specific embodiment, the sacrificial electrode comprises one or more of zinc and magnesium. The sacrificial electrode will be in electrical connection with a first pole or electrode or terminal of the light source, UV emitting device, anti-biofouling system, respectively, and a second electrode (also indicated as "second energy system electrode") of the local energy harvesting system will be in electrical connection with a second pole or electrode or terminal of the light source, UV emitting device, anti-biofouling system, respectively.

In a further embodiment, the second energy system electrode comprises steel iron, such as steel. However, other materials may also be applied, like especially one or more of carbon, graphite, coke, platinum, mill scale on steel, high silicon cast iron, copper, brass, bronze, lead, and cast iron (not graphitized), instead of or in addition to e.g. steel. The phrase "wherein the sacrificial electrode comprises one or more of zinc and magnesium" may also refer to sacrificial electrodes comprising an alloy comprising zinc and/or magnesium. However, the sacrificial electrode may also substantially consist of zinc and/or magnesium. Other materials may also be applied, such as some sorts of aluminum or aluminum alloys.

For example, one copper electrode and one zink electrode, each connected to a different terminal of the LED and both submerged in water, may generate a voltage (and thus current). Once above water, the generation of current will automatically and instantly stop.

In yet further embodiments the UV radiation may be accompanied by warning information. For instance, when the UV radiation is switched on, especially above the water (line), one or more of a sound signal and a light signal may be provided. The sound signal and/or light signal may include warning information, such as spoken text, projected text, or a configuration of light that contains information (similar to a display).

In a specific embodiment, the UV emitting element comprises a luminescent material configured to absorb part of the UV radiation and convert into visible luminescent material light (i.e. visible light generated by the luminescent material upon excitation with the UV radiation), wherein the light source and said luminescent material are configured to provide said visible luminescent material light emanating in a direction away from the external surface. Optionally, the anti-biofouling system is configured to provide said luminescent material light in a pulsed way. Hence, in this way, a person at a distance from the object (and thus external from the object) may perceive the luminescence, e.g. a red blinking light.

Alternatively or additionally, the UV emitting element comprises a second light source configured to provide visible second light source light of which at least part emanates in a direction away from the external surface. Again, optionally the anti-biofouling system may be configured to provide said visible second light source light in a pulsed way. Hence, in this way, a person at a distance from the object (and thus external from the object) may perceive the visible second light source light, e.g. a red blinking light.

In yet a further embodiment, the anti-biofouling system may further be configured to provide visible light emanating as a light beam in a direction away from the external surface, wherein the light beam has a cross-section having the shape of a warning sign. This visible light may in embodiments be provided by one or more of the second light source and the luminescent material. Hence, the second light sources may be configured in a warning signal configuration, which may especially be visible when the second light sources are switched on.

Yet in further embodiments the anti-biofouling system may further comprise a sensor configured to provide a sensor signal indicative for one or more of (i) the sensor being in physical contact with the water and (ii) the part being in physical contact with the water, and a control system, wherein the control system is configured to provide said UV radiation as function of said sensor signal.

Further, one may also take into account the fact that some parts of the object may substantially always be below the water (line). In an embodiment, wherein the object comprises a vessel, the UV radiation escape surface may be configured to the external surface of the object at a position which is permanent under the water (line) during use of the object. For instance, this may be the load line of the vessel at zero load. However, this embodiment may also be applied to infrastructural object. One may however have sometimes to take into account lower levels in the summer (and higher levels in the winter). Note that the fact that the UV radiation escape surface may substantially always below the water (line), this does not imply that the entire anti-biofouling system has to be below the water (line).

A further precautionary measure that may be taken may be related to the direction of the UV radiation. In a specific embodiment the UV emitting element is configured to provide at least 80%, such as at least 90%, or even substantially all, of the power of the UV radiation in a direction within an angle of 0-90° such as within an angle of 0-45° from a perpendicular to the earth's surface and in a direction below the object, relative to the object during its use.

The anti-biofouling system is especially configured to provide UV radiation to the part of the object or to water adjacent to this part. This especially implies that during an irradiation stage the UV radiation is applied. Hence, there may optionally also be periods wherein no UV radiation is applied at al. This may (thus) not only be due to e.g. a control system switching of one or more of the UV emitting elements, but may e.g. also be due to predefined settings such as day and night or water temperature, etc. For instance, in an embodiment the UV radiation is applied in a pulsed way.

Hence, in a specific embodiment or aspect, the anti-biofouling system is configured for preventing or reducing biofouling on a fouling surface of an object, that during use is at least temporarily exposed to water, by providing an anti-fouling light (i.e. UV radiation) to said fouling surface or water adjacent thereto, the anti-fouling lighting system comprising (i) a lighting module comprising (i) a light source configured to generate said anti-fouling light; and (ii) a control system configured to control an intensity of the anti-fouling light as function of one or more of (i) a feedback signal related to a biofouling risk and (ii) a timer for time-based varying the intensity of the anti-fouling light. Especially, the anti-biofouling system may be configured to provide said anti-fouling light via an optical medium to said fouling surface, wherein the lighting module further comprises (ii) said optical medium configured to receive at least part of the UV radiation (anti-fouling light), the optical medium comprising an emission surface configured to provide at least part of said UV radiation (anti-fouling light). Further, especially the optical medium comprises one or more of a waveguide and an optical fiber, and wherein the UV radiation (anti-fouling light) especially comprises one or more of UVB and UVC light. These waveguides and optical media are herein further not discussed in detail.

The optical medium may also be provided as a (silicone) foil for applying to the protected surface, the foil comprising at least one light source for generating anti-fouling light and a sheet-like optical medium for distributing the UV radiation across the foil. In embodiments the foil has a thickness in an order of magnitude of a couple of millimeters to a few centimeters, such as 0.1-5 cm, like 0.2-2 cm. In embodiments, the foil is not substantially limited in any direction perpendicular to the thickness direction so as to provide substantially large foil having sizes in the order of magnitude of tens or hundreds of square meters. The foil may be substantially size-limited in two orthogonal directions perpendicular to the thickness direction of the foil, so as to provide an anti-fouling tile; in another embodiment the foil is substantially size-limited in only one one direction perpendicular to a thickness direction of the foil, so as to provide an elongated strip of anti-fouling foil. Hence, the optical medium, and even also the lighting module, may be provided as tile or as strip. The tile or strip may comprise a (silicone) foil.

In an embodiment the lighting module comprises a two-dimensional grid of light sources for generating UV radiation and the optical medium is arranged to distribute at least part of the UV radiation from the two-dimensional grid of light sources across the optical medium so as to provide a two-dimensional distribution of UV radiation exiting the light emitting surface of the light module. The two-dimensional grid of light sources may be arranged in a chicken-wire structure, a close-packed structure, a rows/columns structure, or any other suitable regular or irregular structure. The physical distance between neighboring light sources in the grid may be fixed across the grid or may vary, for example as a function of light output power required to provide the anti-fouling effect or as function of the location of the lighting module on the protected surface (e.g. location on the hull of a ship). Advantages of providing a two-dimensional grid of light sources include that the UV radiation may be generated close to the areas to be protected with UV radiation illumination, and that it reduces losses in the optical medium or light guide and that it is increasing homogeneity of the light distribution. Preferably, the UV radiation is generally homogeneously distributed across the emission surface; this reduces or even prevents under-illuminated areas, where fouling may otherwise take place, while at the same time reducing or preventing energy waste by over-illumination of other areas with more light than needed for anti-fouling. In an embodiment, the grid is comprised in the optical medium. In yet another embodiment, the grid may be comprised by a (silicone) foil.

Further, in an embodiment the optical medium may be disposed proximate (including optionally attached to) to the protected surface and coupled to receive the ultraviolet light, wherein the optical medium has a thickness direction perpendicular to the protected surface, wherein two orthogonal directions of the optical medium orthogonal to the thickness direction are parallel to the protected surface, wherein the optical medium is configured to provide a propagation path of the ultraviolet light such that the ultraviolet light travels within the optical medium in at least one of the two orthogonal directions orthogonal to the thickness direction, and such that, at points along a surface of the optical medium, respective portions of the ultraviolet light escape the optical medium.

In a further aspect, the invention also provides a method of anti-(bio)fouling (a part of) an external surface of an object that is during use at least temporarily exposed to water, the method comprising: providing the anti-biofouling system as defined herein to the object, generating the UV radiation (during use of the object), optionally as function of one or more of (i) a feedback signal (such as related to biofouling risk and/or a human UV radiation exposure risk), and (ii) a timer for (periodically) varying the intensity of the UV radiation (anti-fouling light), and providing said UV radiation (during an irradiation stage) to (the part of) the external surface. Such feedback signal may be provided by the sensor.

In yet a further aspect, the invention also provides a method of providing an anti-biofouling system to an object, that during use is at least temporarily exposed to water, the method comprising providing, such as integrating in the object and/or attaching to an external surface, the anti-biofouling system to the object, such as a vessel, with the UV emitting element configured to provide said UV radiation to one or more of a part of an external surface of the object and water (being) adjacent to said part (during use). Especially, the UV emitting element is attached to the external surface, or may even be configured as (first) part of the external surface.

The terms "visible", "visible light" or "visible emission" refer to light having a wavelength in the range of about 380-780 nm.

BRIEF DESCRIPTION OF THE DRAWINGS

Embodiments of the invention will now be described, by way of example only, with reference to the accompanying schematic drawings in which corresponding reference symbols indicate corresponding parts, and in which:

FIGS. 2a-2f schematically depict some embodiments and variants;

FIGS. 3a-3b schematically depict some further embodiments and variants;

FIGS. 4a-4e schematically depict some further embodiments and variants; and

FIGS. 5a-5c schematically depict some further embodiments and variants.

The drawings are not necessarily on scale.

DETAILED DESCRIPTION OF THE EMBODIMENTS

Figure 1A:
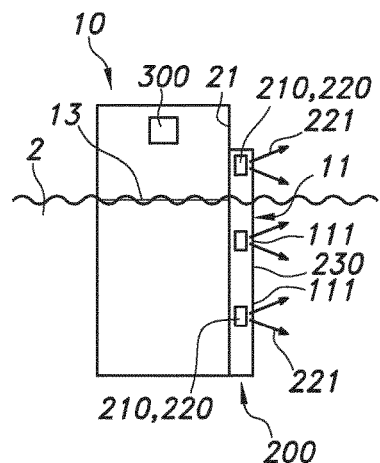
FIGS. 1a-1c schematically depict some general aspects.
Figure 1B:
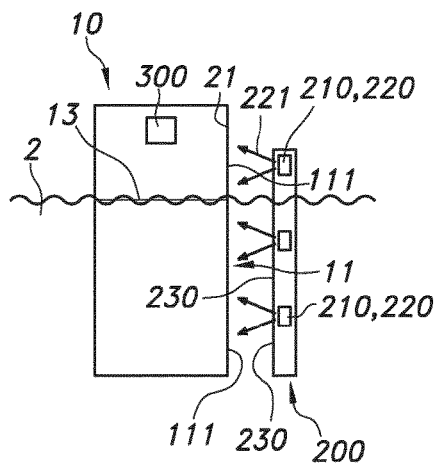

FIGS. 1a-1b schematically depict embodiments of an object 10 that during use is at least partly submerged in water 2, see the water line 13. The object 10, such as a vessel or a sluice, see also below, further comprises an anti-biofouling system 200 comprising an UV emitting element 210, especially for application of UV radiation 221 to a part 111 of an external surface 11 of the object 10, such as a hull or part or a hull. Here, two embodiments are shown wherein the anti-biofouling system 200, or more especially the UV emitting element 210 is part of an outer surface, and thereby forms in fact part of the outer surface (FIG. 1a) or wherein the UV emitting element 210 is configured to irradiate the outer surface and does not necessarily form part of an outer surface, such as a hull of a ship (FIG. 1b). For instance, the object 10 is selected from the group consisting of a vessel 1 and an infrastructural object 15 (see also below).

The UV emitting element 210 comprises one or more light sources 220 and may thus especially be configured to irradiate with said UV radiation 221 during an irradiation stage one or more of (i) said part 111 of said external surface 11 and (ii) water adjacent to said part 111 of said external surface 11. The former variant applies especially the embodiment of FIG. 1b, and the latter embodiment especially applies to both embodiments of FIGS. 1a-1b. Note however that when an external surface of the UV emitting element 210 is configured as external surface of the object 10, of course the part 111 is irradiated per se with the UV radiation 21.

Hence, the UV emitting element 210 comprises a UV radiation escape surface 230 and the UV emitting element 210 is configured to provide said UV radiation 221 downstream from said UV radiation escape surface 230 of said UV emitting element 210.

Especially, the light source 220 is at least controllable between a first UV radiation level and a second UV radiation level, wherein the first UV radiation level is larger than the second UV radiation level (and wherein the second UV radiation level is smaller than the first radiation level (including e.g. zero).

In a specific embodiment, the object 10 further comprises a control system 300 configured to control said UV radiation 221 as function of input information comprising information of one or more of (i) a location of the object 10, (ii) movement of the object 10, (iii) a distance d of the object 10 to a second object 20, and (iv) a position of the part 111 of the external surface 11 relative to the water. This is further elucidated in amongst others FIGS. 2a-2f.

Figure 1C:
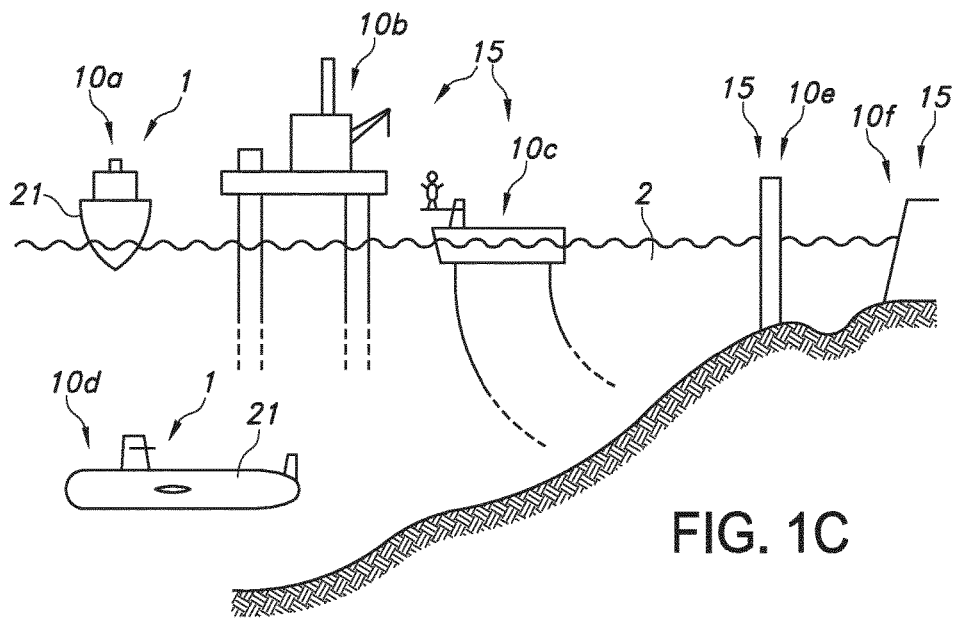

As indicated above, the term "vessel", indicated with reference 1, may e.g. refer to e.g. a boat or a ship (ref 10a in FIG. 1c), etc., such as a sail boat, a tanker, a cruise ship, a yacht, a ferry, a submarine (ref. 10d in FIG. 1c), etc. etc . . . , like schematically indicated in FIG. 1c. The term "infrastructural object", indicated with reference 15, may especially refer to aquatic applications that are in general arranged substantially stationary, such as a dam/sluice (references 10e/10f in FIG. 1c), a pontoon (ref 10c in FIG. 1c), an oilrig (ref. 10b in FIG. 1c), etc. etc.

As indicated above, the object 10 may further comprises a control system 300 configured to control said UV radiation 221 as function of input information comprising information of one or more of (i) a location of the object 10, (ii) movement of the object 10, (iii) a distance (d) of (said part of) the object 10 to a second object 20, and (iv) a position of the part 111 of the external surface 11 relative to the water.

For instance, the location of the object, especially of a vessel 10 may switch on the UV radiation when on open water, whereas the UV emitting element 210 may be switched off in a harbor. Satellite navigation may e.g. be used (for determination of the location of the object). Hence, in an embodiment the control system 300 is configured to control the UV emitting element 210 to the first UV radiation level when the location of the object 10 complies with a first predetermined location, and to the second UV radiation level when the location of the object 10 complies with a second predetermined location.

Alternatively or additionally, the control system 300 may be configured to control the UV emitting element 210 to the first UV radiation level when the object 10 has a velocity of at least a predetermined minimum velocity, and to the second UV radiation level when the velocity of the objects 10 is below said predetermined minimum velocity. A low velocity may indicate a higher likelihood of people in the vicinity of the UV emitting element 210 than a high velocity.

Alternatively or additionally, the control system 300 may be configured to control the UV emitting element 210 to the first UV radiation level when the distance d of the object 10 to the second object 20 meets at least a predefined threshold value, and to the second UV radiation level when the distance d of the object 10 to the second object 20 is below the predefined threshold value. This is schematically depicted in FIG. 2a.

Figure 2A:
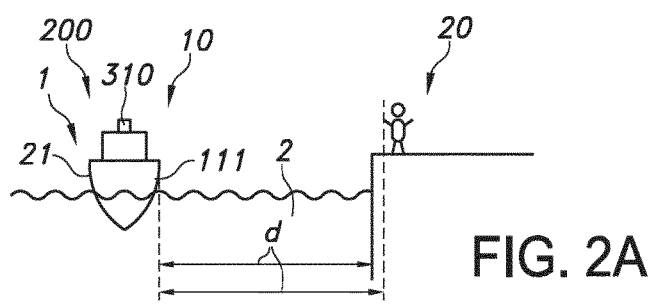

For controlling the UV emitting element 210 as function of one or more of the herein indicated parameters, the object 10 may further comprise a sensor 310, see e.g. FIG. 2a, configured to sense one or more of (i) a second object 20 and (ii) a movement of the second object (20) and configured to generate a corresponding sensor signal. The control system 300 may especially be configured to control said UV radiation 221 as function of said sensor signal. The second object may be stationary or moving. Further the second object may e.g. a human (see the example in FIG. 2a), or non-moving, such as quay (see also FIG. 2a). The sensor may optionally be comprised by the anti-bio-fouling system 200 (see e.g. FIG. 2b.

Figure 2B:
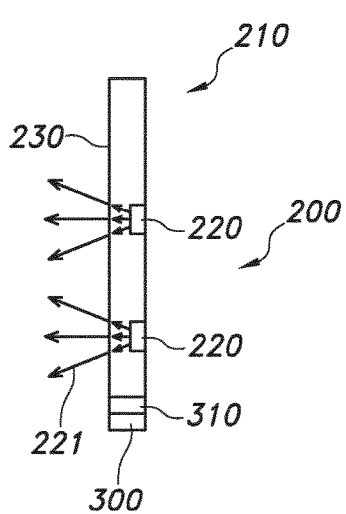

FIG. 2b schematically depicts in more detail an embodiment of the anti-biofouling system 200, here by way of example including an integrated control system 300 and an integrated sensor 310.

Figure 2C:
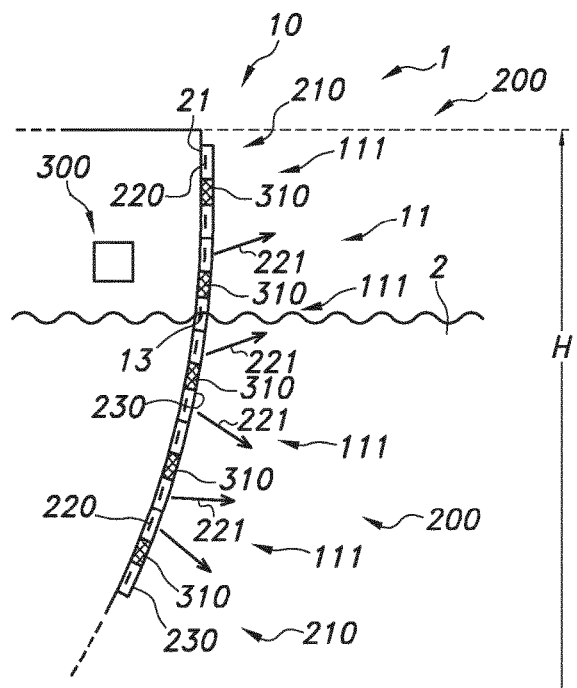

FIG. 2c schematically depicts an external surface 11 of an object 10, such as a vessel wall or a wall of an infrastructural object, with by way of example a plurality UV emitting elements 210 (here associated to a hull 21 of a vessel 1). Alternatively or additionally, a plurality of functionally coupled or independently functioning anti-biofouling systems 200 may be applied.

For instance, assuming a single control system 300, which may e.g. be a master control system with subordinated slave control systems (not depicted), may e.g. be configured to control the UV emitting element 210 to the first UV radiation level when one or more of the part 111 and the UV radiation escape surface 230 are below the water line 13, and to the second UV radiation level when one or more of the part 111 and the UV radiation escape surface 230 are above the water line 13. For instance, all UV emitting elements 210 below the water (line) may be switched on, while all above the water (line) may be switched off. Note that in the schematic drawing 2c also one of the UV emitting elements 210 above the water line 3 is switched, e.g. in the case that the control system decides that it is safe to switch such UV emitting elements 210 on. Use of an additional safeguard, such as a water switch may be used as alternative or additional control (see also below).

FIG. 2c also schematically depicts the embodiment wherein the anti-biofouling system 200 comprises a plurality of UV emitting elements 210 (with a plurality of light sources), a plurality of radiation escape surfaces 230, and a plurality of said parts 111, wherein the plurality of light sources 220 are configured to provide said UV radiation 221 via said plurality of radiation escape surfaces 23 to said plurality of parts 111, and wherein said plurality of parts 111 are configured at different heights of the object 10, and wherein the control system 300 is configured to control the light sources 220 individually as function of said input information. For instance, in an embodiment the control system 300 may be configured to control the light sources 220 individually as function of the positions of the parts 111 of the external surface 11 relative to the water. In a first variant, the input information comprising information of the position of the external surface 11 relative to the water is based on a loading of the vessel 1 (schematically depicted in FIG. 2c). In a second variant, the input information comprising information of the position of the external surface 11 relative to the water is based on a water line relative to the infrastructural object 15.

Figure 2D:
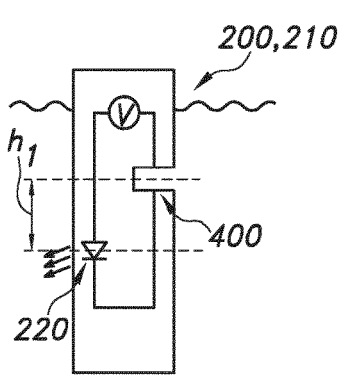

FIG. 2d schematically depicts an embodiment wherein alternatively or additionally the object 10 further comprises a water switch 400, wherein the anti-biofouling system 200 is configured to provide said UV radiation 221 to said part 111 in dependence of the water switch being in physical contact with the water. In FIG. 2d, the water switch is in contact with the water. For instance, by electrical conductivity of seawater, the electric circuit may be closed, by which the light source 220 may provide UV radiation. An anti-biofouling system may comprise one or more of such water switches 400. Optionally, the water switch 400 and light source 220 may be part of a larger circuit with e.g. electronics to amplify the signal, etc. FIG. 2d, like the other drawings, is a schematic drawing.

Figure 2E:
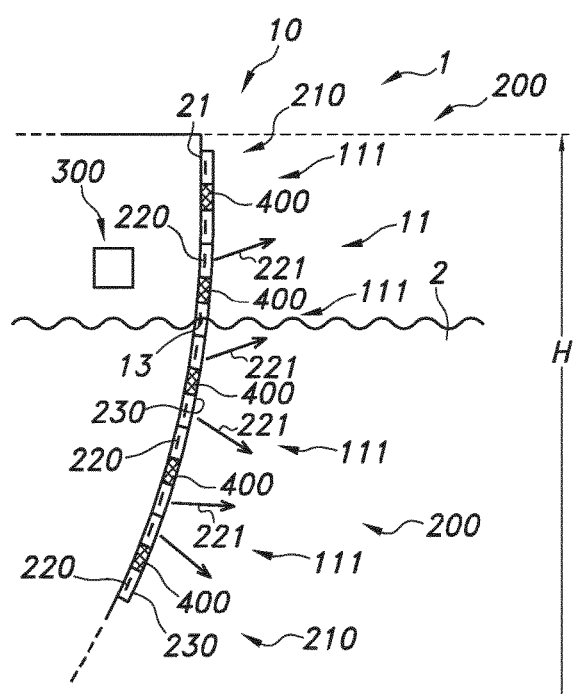

FIG. 2e schematically depicts an embodiment, wherein the anti-biofouling system 200 comprises a plurality of UV emitting elements 210 (with a plurality of light sources), a plurality of radiation escape surfaces 230, and a plurality of said parts 111, wherein the plurality of light sources 220 are configured to provide said UV radiation 221 via said plurality of radiation escape surfaces 230 to said plurality of parts 111, and wherein said plurality of parts 111 are configured at different heights of the object 10, and further comprising a plurality of said water switches 400, configured at the heights of the plurality of parts 111, and wherein the anti-biofouling system 200 is configured to provide said UV radiation 221 to said parts 111 when the respective water switches 400 are in physical contact with the water. Of course, the embodiment of FIG. 2e may optionally be combined with the embodiment schematically depicted in FIG. 2c.

FIG. 2f schematically depicts an embodiment wherein a vessel 1, as embodiment of the object 10, comprises a plurality of anti-biofouling systems 200 and/or a one or more of such anti-biofouling systems 200 comprising a plurality of UV emitting elements 210. Dependent upon the height of the specific such anti-biofouling system 200 and/or the height of the UV emitting elements 210, such as relative to a water (line), the respective UV emitting elements 210 may be switched on.

FIG. 3a schematically depicts an embodiment wherein the object, here especially the anti-biofouling system 200, further comprises a local energy harvesting system 500 configured to harvest electrical energy and to provide said energy to said anti-biofouling system 200. Here, by way of example a turbine is depicted which may provide electrical energy when the vessel is moving in water. Hence, in embodiments the local energy harvesting system 500 is comprised by said anti-biofouling system 200. The local energy harvesting system 500 may e.g. comprise a solar cell, a turbine operating in water, a piezoelectric element operating on a pressure of waves, etc.

Especially, local energy harvesting systems may be applied that upon contact with the water provide electrical energy, especially energy harvesting systems that provide electrical energy when submerged in water and being subjected to a movement of water. FIG. 3b schematically depicts an embodiment wherein dependent upon the height of the specific anti-biofouling system 200 and/or the height of the UV emitting elements 210, such as relative to a the water (line), the respective UV emitting elements 210 may receive electrical energy from the local energy harvesting system 500. Hence, especially the local energy harvesting system 500 may comprise one or more of a turbine operating in water and a piezoelectric element operating on a pressure of waves.

Alternatively or additionally, the local energy harvesting system comprises (i) a sacrificial electrode in electrical connection with a first electrode of the light source 220, and (ii) a second energy system electrode in electrical connection with a second electrode of the light source 220, wherein the energy system is configured to provide electrical power to said anti-biofouling system 200 when the sacrificial electrode and the second energy system electrode are in electrical contact with the water. Also such embodiment may be implemented in the configuration of FIG. 3b (see further for this embodiment FIGS. 5a-5c). Of course, the embodiment of FIG. 3b may optionally be combined with the embodiments schematically depicted in one or more of FIGS. 2c and 2e.

FIG. 4a shows a chicken-wire embodiment where light sources 210, such as UV LEDs, are arranged in a grid and connected in a series of parallel connections. The LEDs can be mounted at the nodes either through soldering, gluing or any other known electrical connection technique for connecting the LEDs to the chicken wires. One or more LEDs can be placed at each node. DC or AC driving can be implemented. If AC is used, then a couple of LEDs in anti parallel configuration may be used. The person skilled in the art knows that at each node more than one couple of LEDs in anti parallel configuration can be used. The actual size of the chicken-wire grid and the distance between UV LEDs in the grid can be adjusted by stretching the harmonica structure. The chicken-wire grid may be embedded in an optical medium. Above, especially active prevention applications are described, wherein the anti-biofouling system 200 switches off, or switches specific UV emitting elements 210 or specific light sources 220 off, dependent upon contact with the water, a signal of a sensor, etc. etc. However, alternatively or additionally, also warning signals or messages may be used to warn a person of danger.

Hence, the invention also provides an object 10 that during use is at least partly submerged in water, the object 10 further comprising an anti-biofouling system 200 comprising an UV emitting element 210, especially for application of UV radiation 221 to a part 111 of an external surface 11 of the object 10, wherein the UV emitting element 210 comprises one or more light sources 220 and is configured to irradiate with said UV radiation 221 during an irradiation stage one or more of (i) said part 111 of said external surface 11 and (ii) water adjacent to said part 111 of said external surface 11, wherein the UV emitting element 210 comprises a UV radiation escape surface 230 and wherein the UV emitting element 210 is configured to provide said UV radiation 221 downstream from said UV radiation escape surface 230 of said UV emitting element 210, with one or more of the functionalities indicated below.

For instance, in an embodiment the UV emitting element 210 comprises a luminescent material 260 configured to absorb part of the UV radiation 221 and to convert into visible light 261, wherein the light source 220 and said luminescent material 260 are configured to provide said visible light 261 (see FIGS. 4a-4b) emanating in a direction away from the external surface 11 (see FIG. 4b). Visible light in general is indicated with reference 291, and luminescent material light in the visible is indicated with reference 261. For instance, alternatively or additionally, the UV emitting element 210 comprises a second light source 280 configured to provide visible second light source light 281, such as especially red light, of which at least part emanates in a direction away from the external surface 11 (see this variant also depicted in FIG. 4a). FIG. 4a schematically depicts a LED grid, that may e.g. be used in the UV emitting element 210 to provide UV radiation 221 (and thus optionally also visible light 291.

In a specific embodiment, schematically depicted in FIGS. 4b and 4d (but optionally implicitly also in FIG. 4c) the anti-biofouling system 200 may further be configured to provide visible light 291 emanating as a light beam 292 in a direction away from the external surface 11, wherein the light beam 292 has a cross-section having the shape of a warning sign. FIG. 4c schematically depicts an arrangement of light sources 280, which may provide such warning signal (see FIG. 4d). Note that FIG. 4c schematically depicts the light sources 280 configured to generate visible light 291 (see FIG. 4d). UV light sources 220 fill the rest of the area. The light source 280 are arranged in a warning signal configuration (and may e.g. lead to the beam shown in FIG. 4d). Note that instead of visible light emitting light sources 280 also UV emitting light sources 220 in combination with a luminescent material may be applied, or a combination of such variants.

In yet a further specific embodiment, the object 10 comprises e.g. a vessel 1, wherein the UV radiation escape surface 230 is configured to the external surface 11 of the object 10 at a position which is permanent under the water (line) during use of the object 10. For instance, assuming a vessel, the UV emitting element(s) may be configured below the tropical fresh water load line (TF), or even below the freshwater load line (F), or below tropical zones load line (T), or yet even below the summer load line (S), or even below the winter load line (W), yet even only below the winter North Atlantic load line (WNA). Hence, in embodiments the freeboard may be kept free from UV radiation (and from UV emitting element(s).

In yet another embodiment, schematically depicted in FIG. 4e the UV emitting element 210 is configured to provide at least 80% of the power of the UV radiation in a direction within an angle θ of 0-90° from a perpendicular P to the earth's surface and in a direction below the object 10, relative to the object during its use 10.

FIGS. 5a-5c schematically depicts some aspects of the anti-biofouling system and its application. It is for instance an aspect of the invention to insert UV LEDs and/or other light sources into an electrical circuit that may already be available in an object 10 having a (steel) external surface 11 and a sacrificial electrode 510 attached thereto, see FIGS. 5a-5c for a comparison between the situation without UV emitting element 210 (FIG. 5a), and with a light source (FIGS. 5b and 5c). The dashed line indicates by way of example an electrical return path through the steel external surface 11. The steel hull 21, here the external surface 11, may act as a second energy source electrode 570. In this way, energy system 500 is provided, that may be used to power a light source or UV emitting element 210. FIG. 5b shows the introduction of a UV emitting element 210 which may illuminate the external surface 11, and which may be powered by the energy system 500.

FIG. 5c schematically depicts in more detail an embodiment of the anti-biofouling system 200 (here also in an embodiment of the closed unit), wherein by way of example the UV emitting element 210 is comprised by an optical medium 270. The anti-biofouling system is further elucidated amongst others with respect to this embodiment, but the invention is not limited to this embodiment. FIG. 5c schematically depicts an anti-biofouling system 200 configured for preventing or reducing (water related) biofouling on a external surface 11 of an object 10 that during use is at least temporarily exposed to an electrically conductive aqueous liquid, by providing an UV radiation (anti-fouling light) 221 to said external surface 11.

Alternatively or additionally, the local energy harvesting system 500 comprises (i) a sacrificial electrode 510 in electrical connection with a first electrode (not shown) of the light source or system 200 or UV emitting element 210, and (ii) a second energy system electrode 570 in electrical connection with a second electrode (not shown) of the light source or system 200 or UV emitting element 210, wherein the energy system 500 is configured to provide electrical power to said anti-biofouling system 200 when the sacrificial electrode 510 and the second energy system electrode 570 are in electrical contact with the water.

Hence, herein optical and/or electrical approaches are suggested to provide extra safety when using UV radiation. One or more of these approaches may be applied simultaneously.

Optical approaches include amongst others:

The use of visible LEDs in series with a UV LED: UV light is harmful to human beings. What makes it more risky, is the fact that it is invisible. This implies that human beings have no visible, audible or any other warning signs when they're exposed to UV light (This also explains why sunburns are common). The safety idea proposed here is to have a visible LED (e.g. bright red) in series with a UV LED. Because of the series connection, the visible LED will "always" be on when the UV LED is on, thus giving a clearly visible warning sign.

The combination of a visible+UV light in direct series connection can be a very fundamental safety building block.

Alternatively or additionally, a number of visible LEDs can be organized in a pattern on the hull of a ship, to e.g. show a warning symbol, like a triangle or exclamation mark.

Another approach is to embed a phosphor in the coating, near the UV source. This phosphor should convert the UV light to a visible light wavelength. Again, the phosphor can be arranged in a pattern that conveys a warning; like above.

Electrical Approached Include Amongst Others:

LEDs switched on only when in contact with water. Different embodiments can be envisioned:

A (temporary) contact with water flips a switch, and the whole system (or subsection) of LEDs stay on (for a pre-determined period of time)

At LED level: a second electrode of the LED is directly connected to the water, implying that a closed circuit is only obtained when the LED is submerged; the water is the return electrode.

Alternatively, the water can close a small gap in the circuit for each individual LED (or section of LEDs).

Further, mechanical and system approaches are proposed herein. One or more of these approaches may be applied simultaneously. With 'system approaches', it is especially meant that the safety of the entire application (such as an entire vessel) is controlled at a system level. That is, the entire system (or large parts or subsections) are controlled at once.

System Approaches Include Amongst Others:

As the UV light is mainly emitted on the lower side (and outside) of the hull, people on board the ship hardly have a line of sight to the UV emitting layers. Hence they are not at risk of UV exposure. This is different for people outside of the boat; most relevant when a boat is docked in harbor. In that scenario, people are walking on the docks, and small supply vessels are sailing around the boat (fuel supply ships etc.).

An embodiment is to use a sensor that detects movement and/or presence (via infrared light, generated by human beings and or small engines of small boats or cars). When movement or presence is detected, the entire UV system (or parts of it) will be switched off (temporarily). The idea is similar, yet opposite, to common household systems, where a light on the outside of a house (i.e. on the porch) is turned ON when presence or motion is detected. We switch our (UV) lights OFF.

Optionally, also a timer may be employed to switch on the light again after a predetermined period of time without movement being detected.

Design approaches include amongst others:

As the absorption of water for UV light is fairly high, only LEDs above the waterline (or within the first ~0.50 m) may emit light that actually reaches human beings (assuming they're above the water line and not swimming around the boat). Hence, only LEDs may be configured on 'deeper' sections of the boat, and/or only turn on the upper sections (close to the waterline) in 'inherently safe' circumstances, like when sailing on the open ocean. This may require the LEDs to be arranged in horizontal, striped sections, of e.g. 1 meter in height, which can be controlled individually. The actually loading of the ship may then be used to decide which sections to turn on.

In a further embodiment the LEDs are only applied on the lowest parts of the boat; that never get above the waterline, not even on an empty vessel.

The layout of the LEDs in the optical structure may be designed such that the light is emitted primarily outwards (as needed for all applications) and downwards. This may not completely eliminate any UV light of "escaping to above the waterline", but it will severely limit the amount.

Hence, safety improvements for an UV based anti-fouling system are proposed. The various embodiments can be used individually and/or in combinations of one or more. Thus, the risk of UV light reaching human eyes may substantially be reduced (to an acceptable level).

The term "substantially" herein, such as in "substantially all light" or in "substantially consists", will be understood by the person skilled in the art. The term "substantially" may also include embodiments with "entirely", "completely", "all", etc. Hence, in embodiments the adjective substantially may also be removed. Where applicable, the term "substantially" may also relate to 90% or higher, such as 95% or higher, especially 99% or higher, even more especially 99.5% or higher, including 100%. The term "comprise" includes also embodiments wherein the term "comprises" means "consists of". The term "and/or" especially relates to one or more of the items mentioned before and after "and/or". For instance, a phrase "item 1 and/or item 2" and similar phrases may relate to one or more of item 1 and item 2. The term "comprising" may in an embodiment refer to "consisting of" but may in another embodiment also refer to "containing at least the defined species and optionally one or more other species".

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

The devices herein are amongst others described during operation. As will be clear to the person skilled in the art, the invention is not limited to methods of operation or devices in operation.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "to comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention further applies to a device comprising one or more of the characterizing features described in the description and/or shown in the attached drawings. The invention further pertains to a method or process comprising one or more of the characterizing features described in the description and/or shown in the attached drawings.

The various aspects discussed in this patent can be combined in order to provide additional advantages. Furthermore, some of the features can form the basis for one or more divisional applications.

The invention claimed is:

1. An object that during use is at least partly submerged in water, the object further comprising an anti-biofouling system comprising an UV emitting element, wherein the UV emitting element is configured to irradiate with UV radiation during an irradiation stage one or more of (i) a part of an external surface of said object and (ii) water adjacent to said part of said external surface, wherein the light source is at least controllable between a first UV radiation level and a second UV radiation level, wherein the first UV radiation level is larger than the second UV radiation level, wherein the object is selected from the group consisting of a vessel and an infrastructural object, wherein the object further comprises a control system configured to control said UV radiation as function of input information comprising information of one or more of (i) a location of the object, (ii) movement of the object, (iii) a distance (d) of the object to a second object, and (iv) a position of the part of the external surface relative to the water.

2. The object according to claim 1, wherein the control system is configured to control the UV emitting element to the first UV radiation level when the location of the object complies with a first predetermined location, and to the second UV radiation level when the location of the object complies with a second predetermined location.

3. The object according to claim 1, wherein the control system is configured to control the UV emitting element to the first UV radiation level when the object has a velocity of at least a predetermined minimum velocity, and to the second UV radiation level when the velocity of the objects is below said predetermined minimum velocity.

4. The object according to claim 1, wherein the control system is configured to control the UV emitting element to the first UV radiation level when the distance (d) of the object to the second object meets at least a predefined threshold value, and to the second UV radiation level when the distance (d) of the object to the second object is below the predefined threshold value.

5. The object according to claim 1, further comprising a sensor configured to sense one or more of (i) the presence of a second object and (ii) a movement of the second object and configured to generate a corresponding sensor signal, and wherein the control system is configured to control said UV radiation as function of said sensor signal.

6. The object according to claim 1, wherein the control system is configured to control the UV emitting element to the first UV radiation level when the part is below the water, and to the second UV radiation level when the part is above the water.

7. The object according to claim 1, wherein the UV emitting element comprises a UV radiation escape surface and wherein the UV emitting element is configured to provide said UV radiation downstream from said UV radiation escape surface of said UV emitting element, wherein the anti-biofouling system comprises a plurality of light sources, a plurality of radiation escape surfaces, and a plurality of said parts, wherein the plurality of light sources are configured to provide said UV radiation via said plurality of radiation escape surfaces to said plurality of parts, and wherein said plurality of parts are configured at different heights of the object, and wherein the control system is configured to control the light sources individually as function of said input information.

8. The object according to claim 7, wherein the control system is configured to control the light sources individually as function of the positions of the parts of the external surface relative to the water.

9. The object according to claim 1, wherein the input information comprising information of the position of the external surface relative to the water is based on a loading of the vessel.

10. The object according to claim 1, wherein the input information comprising information of the position of the external surface relative to the water is based on a water line relative to the infrastructural object.

11. The object according to claim 1, wherein the UV emitting element comprises a UV radiation escape surface and wherein the UV emitting element is configured to provide said UV radiation downstream from said UV radiation escape surface of said UV emitting element, wherein the radiation escape surface of the anti-biofouling system is configured as part of said external surface.

12. The object according to claim 1, wherein the object comprises a vessel comprising a hull, and wherein the UV emitting element is attached to said hull.

13. The object according to claim 1, wherein one or more of (i) the anti-biofouling system is further configured to provide visible light emanating as a light beam in a direction away from the external surface, and wherein the light beam has a cross-section having the shape of a warning sign, and (ii) the UV emitting element comprises a second light source configured to provide visible second light source light of which at least part emanates in a direction away from the external surface, applies.

14. The object according to claim 1, wherein the UV emitting element comprises a UV radiation escape surface and wherein the UV emitting element is configured to provide said UV radiation downstream from said UV radiation escape surface of said UV emitting element, and wherein the part comprises said radiation escape surface.

15. A method of providing an anti-biofouling system as defined in claim 1 to an object, that during use is at least temporarily exposed to water, the method comprising providing the anti-biofouling system to the object with the UV emitting element configured to provide said UV radiation to one or more of a part of an external surface of the object and water adjacent to said part.

\* \* \* \* \*